(12) United States Patent
Kozup et al.

(10) Patent No.: US 9,452,382 B2
(45) Date of Patent: Sep. 27, 2016

(54) TWO STAGE CONTACT COOLER

(71) Applicant: UOP LLC, Des Plaines, IL (US)

(72) Inventors: Steven C. Kozup, Chicago, IL (US);
Paul C. Steacy, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 185 days.

(21) Appl. No.: 14/281,294

(22) Filed: May 19, 2014

(65) Prior Publication Data

US 2015/0329446 A1    Nov. 19, 2015

(51) Int. Cl.
*B01F 3/04*       (2006.01)
*B01D 53/18*      (2006.01)
*C07C 7/11*       (2006.01)
*C07C 5/327*      (2006.01)
*B01D 53/00*      (2006.01)

(52) U.S. Cl.
CPC ............. *B01D 53/18* (2013.01); *B01D 53/185* (2013.01); *B01F 3/04021* (2013.01); *B01F 3/04078* (2013.01); *B01F 3/04468* (2013.01); *C07C 5/327* (2013.01); *C07C 7/11* (2013.01); *B01D 53/002* (2013.01); *B01D 2256/24* (2013.01); *B01D 2257/702* (2013.01)

(58) Field of Classification Search
CPC .. B01F 3/04; B01F 3/04007; B01F 3/04021; B01F 3/04078; B01F 3/04468; B01F 3/04996
USPC ................ 261/115, 117, 34.1, 36.1; 423/210
See application file for complete search history.

(56) References Cited

U.S. PATENT DOCUMENTS 8,518,156 B2 *  8/2013  Kozak ................ B01D 53/1425
                                                    95/156

OTHER PUBLICATIONS

U.S. Appl. No. 14/281,349, Kozup, filed May 19, 2014.

* cited by examiner

*Primary Examiner* — Robert A Hopkins

(57) ABSTRACT

An apparatus and process is disclosed for the cooling of a reactor effluent gas stream. The apparatus includes a two stage contact cooling system with a first stage wash zone and second stage wash zone. Each wash zone has a packed bed, or other type of mechanical system for contacting the gas stream with the cooling liquid. The liquid in the first stage will remove heavy components, allowing for a cleaner second stage that can be reduced in size.

16 Claims, 1 Drawing Sheet

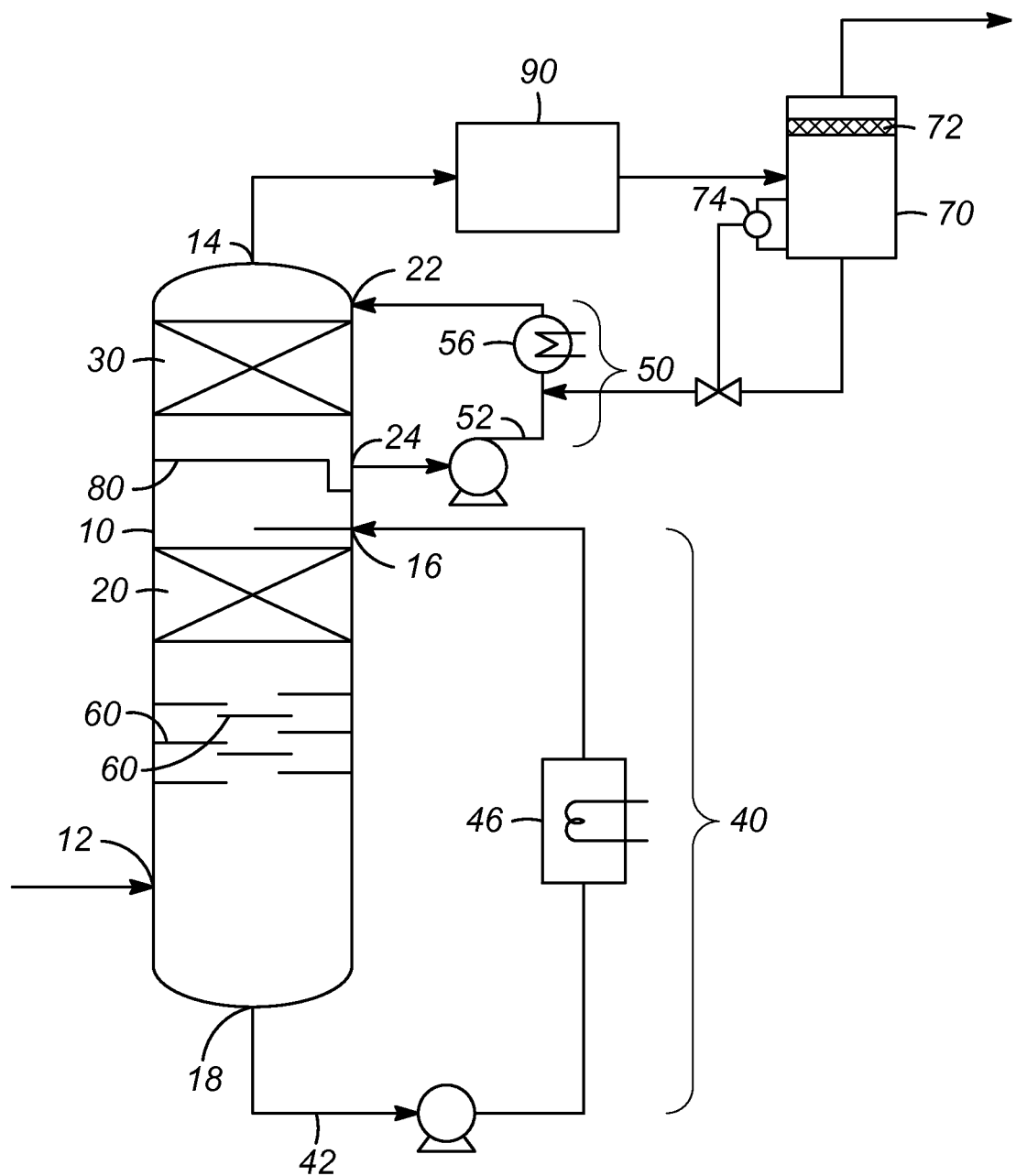

TWO STAGE CONTACT COOLER

FIELD OF THE INVENTION

The field of the invention is related to contact coolers. In particular, the invention is related to contact cooling equipment for use with the cooling of process streams from hydrocarbon processing units.

BACKGROUND

Light olefins, such as ethylene and propylene, are important commercial precursors for a number of products. Most notably the manufacture of polyethylene and propylene, but also as contributing precursors for products such as cumene.

The production of light olefins is generally through cracking of petroleum streams, such as catalytic or steam cracking of a naphtha stream. Light olefins can also be generated by other hydrocarbon processes. The production of light olefins produces by-products from the processes, and the light olefins product streams need to be of a high purity for producing high quality plastic products.

The processing of hydrocarbons generally goes through several stages. The processing steps can be expensive, so reducing cost to improve the economics is important for the production of these products. There is a continuous need for searching for new equipment designs and process to lower the cost of production.

SUMMARY

The present invention comprises an apparatus for cooling a reactor effluent gas comprising olefins, comprising a vessel having a gas inlet, a gas outlet, a first and a second recirculating wash stream outlet, and a first and a second recirculating wash stream inlet; a first packing section disposed within the vessel for contacting the reactor effluent gas with a first wash stream; and a second packing section disposed within the vessel and above the first packing section for contacting the reactor effluent gas leaving the first packing section with a second wash stream.

A second embodiment of the invention comprises an apparatus for cooling a reactor effluent gas comprising olefins, comprising a vessel having a gas inlet, a gas outlet, a recirculating wash stream outlet, and a recirculating wash stream inlet; a packing section disposed within the vessel for contacting the reactor effluent gas with a first wash stream; and a plurality of disc and donut trays disposed within the vessel and below the packing section and above the gas inlet.

An embodiment of the invention is a process for cooling the effluent from a dehydrogenation reactor comprising passing a reactor effluent gas comprising olefins to a contact cooler to generate a cooled effluent stream; passing a first wash oil stream to flow over a first packing section and to contact the reactor effluent gas to generate an intermediate cooled gas effluent stream; and passing a second wash oil stream to flow over a second packing section and to contact the intermediate cooled gas effluent stream to generate the cooled gas effluent stream.

Other objects, advantages and applications of the present invention will become apparent to those skilled in the art from the following detailed description and drawings.

BRIEF DESCRIPTION OF THE DRAWING

The FIGURE shows the apparatus for the two-stage contact cooler of the present invention.

DETAILED DESCRIPTION

The processing of hydrocarbons generally goes through several stages. After a process stream containing a desired product, such as light olefins, is generated, the process stream needs to be purified and cooled. The cooling process can be combined with a wash process to remove impurities, as well as cooling the process stream. Cooling the process stream reduces thermal reactions that can occur should the process stream be maintained at a high temperature. The processing of hydrocarbons often includes side reactions that generate some undesired products. The present invention is a process and apparatus for treating the effluent stream from a dehydrogenation reactor, and in particular, the effluent from a reactor for converting propane to propylene, or isobutane to isobutylene. However, it is not intended to be solely restricted to adding onto to these reactors.

Contact coolers can also be used to remove heavy by-products from a reactor effluent stream in a light olefin generation process. A traditional design recirculates a washing oil, or heavy hydrocarbon stream, collected at the bottoms of a contact cooling vessel, and passed back to the top of the contact cooling vessel. This limits the ability to remove heavies from the reactor effluent stream, which can result in heavies being carried to downstream processing equipment and fouling that downstream equipment. A current design circulates the wash oil, but has a drag stream removing a portion of the circulating oil, and a fresh stream of new oil added to the circulation. This does not, however, prevent all heavies from being removed from the process stream, and therefore allows for some carryover of heavies. Typically, the fresh stream and drag stream have flow rates about 0.5 to 1% of the mass flow of the circulating stream. Important equipment to protect includes downstream compressors, heat exchangers and adsorbent beds.

The present invention provides for a contact cooler with at least two sections, with each section having a separate circulation loop of wash oil. The two sections include a first lower section for cooling and contacting the effluent gas stream to remove heavies, and the second upper section circulates a separate loop of wash oil. The wash oil in the second upper section is cleaner providing a final contact stage for cooling and further reducing any heavies that pass through the first stage.

One embodiment, as shown in the FIGURE, the contact cooler includes a vessel 10 having a gas inlet 12, a gas outlet 14, a first recirculating wash stream inlet 16, a first recirculating wash stream outlet 18, a second recirculating wash stream inlet 22 and a second recirculating wash stream outlet 24. The contact cooler 10 includes a first packing section 20 disposed within the vessel 10 and a second packing section 30 disposed within the vessel above the first packing section 20. The first packing section 20 includes a first recirculating wash system 40 and a second recirculating wash system 50.

The first circulating wash system 40 has a first conduit 42 with an inlet in fluid communication with the first recirculating wash stream outlet 18, and the first conduit 42 with an outlet in fluid communication with the first recirculating wash stream inlet 16. The first recirculating wash system 40 includes a heat exchanger 46 in thermal communication with the first conduit 42. The second circulating wash system 50 has a second conduit 52 with an inlet in fluid communication with the second recirculating wash stream outlet 24, and the second conduit 52 with an outlet in fluid communication with the second recirculating wash stream inlet 22. The second recirculating wash system 50 includes a heat exchanger 56 in thermal communication with the second conduit 52.

The contact cooler can include a plurality of disc and donut trays 60 disposed within the vessel 10 and below the first packing section 20. In one embodiment, the first packing section 20 comprises a bed of packing material having a depth from 1 to 3 meters. The second packing section 30 comprises a bed of packing material having a depth from 1 to 3 meters. Any appropriate inert packing material can be used, including typical packing materials such as Raschig rings, slotted rings, Pall rings, ceramic Berl saddles, structured packing materials, such as structured trays, and other packing materials known in the art.

In one embodiment, the contact cooler includes a discharge drum 70 having an inlet in communication with the vessel gas outlet 14. Disposed within the discharge drum 70 is a demister pad 72 and a level controller 74 for passing recovered wash stream liquid back to the second cooling loop 50.

The contact cooler can includes a filter system disposed within the first conduit 42, for removing solids, settled materials, or heavy components that can be adsorbed on a filter.

The contact cooler further includes a collection tray 80 disposed between the first packing section 20 and the second packing section 30. The collection tray 80 is disposed below the second recirculation wash stream outlet 24, or has a channel disposed below the second recirculation wash stream outlet 24. The collection tray 80 allows the passage of vapor up through the contact cooler, while collecting the second recirculation wash liquid descending from the second packing section 30.

The contact cooler can further include a compressor and a heat exchanger 90 for condensing some of the second recirculating wash fluid. The compressor inlet is in fluid communication with the gas outlet 14 of the vessel 10. The compressor outlet passes the compressed gas to a cooler to condense wash fluid that has been vaporized in the vessel, and the cooled and compressed gas is in fluid communication with the discharge drum 70.

Another embodiment of the present invention is a process for cooling an effluent gas from a dehydrogenation reactor. The process includes passing a reactor effluent gas having olefins, light gases, and heavies generated in the dehydrogenation reactor. The effluent gas is passed to a first wash zone, where the effluent gas is contacted with a first wash oil stream. The effluent gas and wash oil are intermingled in the first wash zone within a first packing section, to generate an intermediate gas stream. The intermediate gas stream is passed to a second wash zone the comprises a second packing section. A second wash oil stream is passed over the second packing section where the second wash oil and intermediate gas stream intermingle to generate a cooled gas effluent with reduced heavies. The cooled effluent gas is passed out of the contact cooling vessel.

The first wash oil stream is collected at the bottom of the contact cooling vessel, and can be filtered to removed heavies and other materials generated or carried over in the process. The first wash oil is cooled and passed up to a distributor over the first packing section to continue the first stage of contact cooling.

The second wash oil stream is collected at a collection tray disposed between the first packing section and the second packing section. The second wash oil stream is cooled and passed to a distributor over the second packing section.

The first wash oil stream and the second wash oil stream preferably are selected from oils having a relatively low volatility to minimize oil carried out in the effluent gas stream. Thus, the cooled effluent gas is compressed and further cooled, and the compressed effluent gas is passed to a discharge drum, where any condensed wash oil is collected. This is likely to be a lighter fraction of the wash oil.

The second wash zone can operate with a lower wash oil rate than the first wash zone. This decreases the size of the second wash zone pump, and will also reduce the circulation rate of the second wash zone oil relative to the circulation rate of the first wash zone oil.

EXAMPLE

An example for the two stage contact cooler can be seen with a system that generates a typical amount of gas. In this example, the effluent gas stream from the dehydrogenation reactor is about 64,000 kg/hr. The first stage wash zone includes a circulating oil at about 118,000 kg/hr. The second stage wash zone includes a circulating oil at about 20,000 kg/hr. The first stage wash zone will have an oil wash rate of about 3.4 l/m2/s (5 gpm/ft2), and the second stage wash zone will have an oil wash rate of about 0.58 l/m2/s. This provides for the second wash zone to have a pump less than 20% of the size of the first wash zone pump for circulating the wash oil. The second wash zone will also have a cleaner wash oil due to the heavies and soluble materials removed in the first wash zone.

The effluent vapor will carry over about 150 kg/hr of wash oil from the second wash zone, and can be collected in the discharge drum, and returned to the second wash oil recirculation system.

Fresh wash oil can be added to the second wash oil recirculation system to make up for losses. In this example about 540 kg/hr is added. Some of the wash oil in the second circulation system will trickle down to the first wash zone, and the first wash zone can have a bleed for passing a portion of the spent wash oil containing heavies. In this example, approximately 514 kg/hr of spent wash oil is removed from the first wash oil recirculation system.

The packing depth of a current single stage contact cooler will typically be about 6 meters. The present invention will reduce the packing depth of each wash zone packing bed to about 2 meters.

SPECIFIC EMBODIMENTS

While the following is described in conjunction with specific embodiments, it will be understood that this description is intended to illustrate and not limit the scope of the preceding description and the appended claims.

A first embodiment of a contact cooler for cooling a reactor effluent gas comprising olefins, comprising a vessel having a gas inlet, a gas outlet, a first and a second recirculating wash stream outlet, and a first and a second recirculating wash stream inlet; a first packing section disposed within the vessel for contacting the reactor effluent gas with a first wash stream; and a second packing section disposed within the vessel and above the first packing section for contacting the reactor effluent gas leaving the first packing section with a second wash stream. An embodiment of the invention is one, any or all of prior embodiments in this paragraph up through the first embodiment in this paragraph further comprising a first cooling loop comprising a first conduit, the first conduit having a first conduit inlet in communication with the first recirculating wash stream outlet and the first conduit having a first conduit outlet in communication with the first recirculating wash stream inlet; and a heat exchanger in thermal communication with the first conduit. An embodiment of the invention is one, any or all of prior embodiments in this paragraph up through the first embodiment in this paragraph further comprising a second cooling loop comprising a second conduit, the second conduit having a second conduit inlet in communication with the second recirculating wash stream outlet and the second conduit having a second conduit outlet in communication with the second recirculating wash stream inlet; and a heat exchanger in thermal communication with the second conduit. An embodiment of the invention is one, any or all of prior embodiments in this paragraph up through the first embodiment in this paragraph further comprising a plurality of disc and donut trays disposed within the vessel and below the first packing section. An embodiment of the invention is one, any or all of prior embodiments in this paragraph up through the first embodiment in this paragraph further comprising a discharge drum having an inlet in communication with the vessel gas outlet, wherein the discharge drum includes a demister pad, and a level controller for passing the wash stream fluid back to the second cooling loop. An embodiment of the invention is one, any or all of prior embodiments in this paragraph up through the first embodiment in this paragraph wherein the first packing section comprises a bed of packing material having a depth from 1 to 3 meters. An embodiment of the invention is one, any or all of prior embodiments in this paragraph up through the first embodiment in this paragraph wherein the second packing section comprises a bed of packing material having a depth from 1 to 3 meters. An embodiment of the invention is one, any or all of prior embodiments in this paragraph up through the first embodiment in this paragraph wherein the first cooling loop further comprises a filter system disposed within the first conduit. An embodiment of the invention is one, any or all of prior embodiments in this paragraph up through the first embodiment in this paragraph further comprising a collection tray disposed between the first and second packing sections, and below the second recirculation wash stream outlet. An embodiment of the invention is one, any or all of prior embodiments in this paragraph up through the first embodiment in this paragraph further comprising a compressor having a compressor inlet in communication with the contact cooler gas outlet, and a compressor outlet. An embodiment of the invention is one, any or all of prior embodiments in this paragraph up through the first embodiment in this paragraph further comprising a distribution tray disposed within the vessel, above the second packing section and below the second recirculating wash stream inlet.

A second embodiment of the contact cooler for cooling a reactor effluent gas comprising olefins, comprising a vessel having a gas inlet, a gas outlet, a recirculating wash stream outlet, and a recirculating wash stream inlet; a packing section disposed within the vessel for contacting the reactor effluent gas with a first wash stream; and a plurality of disc and donut trays disposed within the vessel and below the packing section and above the gas inlet. An embodiment of the invention is one, any or all of prior embodiments in this paragraph up through the first embodiment in this paragraph further comprising a discharge drum having an inlet in communication with the vessel gas outlet, wherein the discharge drum includes a demister pad, and a level controller for passing the wash stream fluid back to the vessel at a position above the packing section. An embodiment of the invention is one, any or all of prior embodiments in this paragraph up through the first embodiment in this paragraph further comprising a cooling loop comprising a conduit, the conduit having a conduit inlet in communication with the recirculating wash stream outlet and the conduit having a conduit outlet in communication with the recirculating wash stream inlet; and a heat exchanger in thermal communication with the conduit. An embodiment of the invention is one, any or all of prior embodiments in this paragraph up through the first embodiment in this paragraph wherein the cooling loop further comprises a filter system disposed within the conduit. An embodiment of the invention is one, any or all of prior embodiments in this paragraph up through the first embodiment in this paragraph wherein the packing section comprises a bed of packing material having a depth from 1 to 3 meters. An embodiment of the invention is one, any or all of prior embodiments in this paragraph up through the first embodiment in this paragraph wherein the packing section comprises a bed of packing material having a depth from 1.5 to 2.5 meters. An embodiment of the invention is one, any or all of prior embodiments in this paragraph up through the first embodiment in this paragraph further comprising a distribution tray disposed within the vessel, above the packing section and below the recirculating wash stream inlet.

An embodiment of the invention includes a process for cooling the effluent from a dehydrogenation reactor comprising passing a reactor effluent gas comprising olefins to a contact cooler to generate a cooled effluent stream; passing a first wash oil stream to flow over a first packing section and to contact the reactor effluent gas to generate an intermediate cooled gas effluent stream; and passing a second wash oil stream to flow over a second packing section and to contact the intermediate cooled gas effluent stream to generate the cooled gas effluent stream. An embodiment of the invention is one, any or all of prior embodiments in this paragraph up through the first embodiment in this paragraph wherein the first wash oil stream and the second wash oil stream comprise an oil having a relatively low volatility.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A contact cooler for cooling a reactor effluent gas comprising olefins, comprising:
   a vessel having a gas inlet, a gas outlet, a first and a second recirculating wash stream outlet, and a first and a second recirculating wash stream inlet;
   a first packing section disposed within the vessel for contacting the reactor effluent gas with a first wash stream;
   a second packing section disposed within the vessel and above the first packing section for contacting the reactor effluent gas leaving the first packing section with a second wash stream; and a compressor having a compressor inlet in communication with the contact cooler gas outlet, and a compressor outlet.

2. The contact cooler of claim 1 further comprising a first cooling loop comprising:
a first conduit, the first conduit having a first conduit inlet in communication with the first recirculating wash stream outlet and the first conduit having a first conduit outlet in communication with the first recirculating wash stream inlet; and
a heat exchanger in thermal communication with the first conduit.

3. The contact cooler of claim 1 further comprising a second cooling loop comprising:
a second conduit, the second conduit having a second conduit inlet in communication with the second recirculating wash stream outlet and the second conduit having a second conduit outlet in communication with the second recirculating wash stream inlet; and
a heat exchanger in thermal communication with the second conduit.

4. The contact cooler of claim 1 further comprising a plurality of disc and donut trays disposed within the vessel and below the first packing section.

5. The contact cooler of claim 3 further comprising:
a discharge drum having an inlet in communication with the vessel gas outlet, wherein the discharge drum includes a demister pad, and a level controller for passing the wash stream fluid back to the second cooling loop.

6. The contact cooler of claim 1 wherein the first packing section comprises a bed of packing material having a depth from 1 to 3 meters.

7. The contact cooler of claim 1 wherein the second packing section comprises a bed of packing material having a depth from 1 to 3 meters.

8. The contact cooler of claim 2 wherein the first cooling loop further comprises a filter system disposed within the first conduit.

9. The contact cooler of claim 1 further comprising a collection tray disposed between the first and second packing sections, and below the second recirculation wash stream outlet.

10. The contact cooler of claim 1 further comprising a distribution tray disposed within the vessel, above the second packing section and below the second recirculating wash stream inlet.

11. A contact cooler for cooling a reactor effluent gas comprising olefins, comprising
a vessel having a gas inlet, a gas outlet, a recirculating wash stream outlet, and a recirculating wash stream inlet;
a packing section disposed within the vessel for contacting the reactor effluent gas with a first wash stream;
a plurality of disc and donut trays disposed within the vessel and below the packing section and above the gas inlet; and
a discharge drum having an inlet in communication with the vessel gas outlet, wherein the discharge drum includes a demister pad, and a level controller for passing the wash stream fluid back to the vessel at a position above the packing section.

12. The contact cooler of claim 11 further comprising a cooling loop comprising:
a conduit, the conduit having a conduit inlet in communication with the recirculating wash stream outlet and the conduit having a conduit outlet in communication with the recirculating wash stream inlet; and
a heat exchanger in thermal communication with the conduit.

13. The contact cooler of claim 12 wherein the cooling loop further comprises a filter system disposed within the conduit.

14. The contact cooler of claim 11 wherein the packing section comprises a bed of packing material having a depth from 1 to 3 meters.

15. The contact cooler of claim 14 wherein the packing section comprises a bed of packing material having a depth from 1.5 to 2.5 meters.

16. The contact cooler of claim 11 further comprising a distribution tray disposed within the vessel, above the packing section and below the recirculating wash stream inlet.

* * * * *